United States Patent
Yang et al.

(10) Patent No.: US 10,342,537 B2
(45) Date of Patent: Jul. 9, 2019

(54) SURGICAL INSTRUMENT AND ITS BENDING CONTROL MECHANISM

(71) Applicants: SHANGHAI YISI MEDICAL TECHNOLOGY CO., LTD., Shanghai (CN); YISI (SUZHOU) MEDICAL TECHNOLOGY CO., LTD., Suzhou, Jiangsu (CN)

(72) Inventors: Guang Yang, Shanghai (CN); Honglin Nie, Shanghai (CN); Anhua Li, Shanghai (CN); Xiliang Zhang, Shanghai (CN); Xiufeng Shi, Shanghai (CN)

(73) Assignees: SHANGHAI YISI MEDICAL TECHNOLOGY CO., LTD., Shanghai (CN); YISI#SUZHOU#MEDICAL TECHNOLOGY CO., LTD., Suzhou, Jiangsu (CN)

( * ) Notice: Subject to any disclaimer, the term of this patent is extended or adjusted under 35 U.S.C. 154(b) by 231 days.

(21) Appl. No.: 15/534,925

(22) PCT Filed: Sep. 22, 2015

(86) PCT No.: PCT/CN2015/090207
§ 371 (c)(1),
(2) Date: Jun. 9, 2017

(87) PCT Pub. No.: WO2016/115917
PCT Pub. Date: Jul. 28, 2016

(65) Prior Publication Data
US 2017/0340327 A1 Nov. 30, 2017

(30) Foreign Application Priority Data

Jan. 19, 2015 (CN) .......................... 2015 1 0026576

(51) Int. Cl.
*A61B 17/072* (2006.01)
*A61B 17/068* (2006.01)
(Continued)

(52) U.S. Cl.
CPC ...... *A61B 17/07207* (2013.01); *A61B 17/068* (2013.01); *A61B 17/00234* (2013.01);
(Continued)

(58) Field of Classification Search
CPC ................ A61B 17/068; A61B 17/072; A61B 17/07207; A61B 17/115;
(Continued)

(56) References Cited

U.S. PATENT DOCUMENTS

5,704,534 A * 1/1998 Huitema .......... A61B 17/07207
227/175.1
5,713,505 A * 2/1998 Huitema .......... A61B 17/07207
227/175.1
(Continued)

*Primary Examiner* — Scott A Smith (57) ABSTRACT

A bending control mechanism includes a turning power input mechanism, a turning transmission mechanism, a locking mechanism and a linear power output mechanism. The turning power input mechanism and the turning transmission mechanism which are coaxially arranged have a relative rotating angle range in the circumferential direction; the turning power input mechanism sequentially rotates in an angle I, an angle range II and an angle III while rotating relative to the turning transmission mechanism from one end angle to the other end angle of a relative rotating angle range, wherein the angle I or the angle III corresponds to turning; the angle range II corresponds to a locking state. With the adoption of the mechanism, the problem of turning and fixing of the surgical instrument in a human body during surgery is solved, and the risk of surgery is reduced.

15 Claims, 8 Drawing Sheets

(51) Int. Cl.
*A61B 17/00* (2006.01)
*A61B 17/29* (2006.01)
*A61B 17/28* (2006.01)

(52) U.S. Cl.
CPC ......... *A61B 17/072* (2013.01); *A61B 17/2833* (2013.01); *A61B 2017/003* (2013.01); *A61B 2017/07214* (2013.01); *A61B 2017/2912* (2013.01); *A61B 2017/2923* (2013.01); *A61B 2017/2927* (2013.01); *A61B 2017/2946* (2013.01)

(58) Field of Classification Search
CPC .. A61B 2017/07214; A61B 2017/2923; A61B 2017/2927; A61B 2017/2929; A61B 2017/2946; A61B 17/00234; A61B 2017/2932
USPC .............. 227/19, 175.1, 175.2, 176.1, 180.1; 606/139, 153, 219
See application file for complete search history.

(56) References Cited

U.S. PATENT DOCUMENTS

| | | | | |
|---|---|---|---|---|
| 5,823,066 A | * | 10/1998 | Huitema | A61B 17/07207 74/527 |
| 7,624,902 B2 | * | 12/2009 | Marczyk | A61B 17/07207 227/175.1 |
| 7,648,055 B2 | * | 1/2010 | Marczyk | A61B 17/072 227/175.1 |
| 8,061,576 B2 | * | 11/2011 | Cappola | A61B 17/072 227/175.1 |
| 8,132,706 B2 | * | 3/2012 | Marczyk | A61B 17/07207 227/175.1 |
| 8,336,754 B2 | * | 12/2012 | Cappola | A61B 17/068 227/175.2 |
| 8,608,045 B2 | * | 12/2013 | Smith | A61B 17/07207 227/175.2 |
| 8,636,766 B2 | * | 1/2014 | Milliman | A61B 17/07207 606/219 |
| 8,789,741 B2 | * | 7/2014 | Baxter | A61B 17/07207 227/180.1 |
| 2013/0075444 A1 | * | 3/2013 | Cappola | A61B 17/068 227/175.2 |

* cited by examiner

SURGICAL INSTRUMENT AND ITS BENDING CONTROL MECHANISM

CROSS REFERENCE OF RELATED APPLICATION

This is a U.S. National Stage under 35 U.S.C 371 of the International Application PCT/CN2015/090207, filed Sep. 22, 2015, which claims priority under 35 U.S.C. 119(a-d) to CN 201510026576.X, filed Jan. 19, 2015.

BACKGROUND OF THE PRESENT INVENTION

Field of Invention

The invention relates to a bending control mechanism for surgical stapler, and more particularly to a mechanism for controlling turning and locking the jaw of the endoscopic stapler.

Description of Related Arts

The action principle of surgical stapler is as follows: two corresponding jaws (commonly referred to as anvil assembly and cartridge assembly) are closed to clamp tissue; and then metal suturing nails in cartridge of the stapler are pushed out to perform molding, to sew tissue together. Some staplers are provided with a cutting knife, to cut off the sewn tissue together.

With the progress of technology, the traditional mode of operation is gradually turned into the endoscopic surgery. In the endoscopic surgery, a number of small incisions with diameter of 5-12 mm are made in different parts of the abdomen or chest; camera lens and a variety of special surgical instruments are inserted in these small incisions; images of various organs in the abdominal cavity taken by the camera inserted in the abdominal cavity are transmitted to the TV screen; by observing the images, the surgeon operates a variety of surgical instruments to complete the operation.

Wherein, the endoscopic stapler plays the most crucial role in the operation. Due to the limitation of space in the abdominal cavity or thoracic cavity, in some extreme cases, the traditional linear endoscopic stapler is unable to effectively reach the surgical site to perform clamping, transection and anastomosis of tissue; therefore, an elbow stapler with stapler jaw (including anvil assembly and cartridge assembly) capable of turning is required. In a straight line state, this kind of elbow stapler capable of turning enters the thoracic cavity or abdominal cavity through puncture outfit; the jaw is controlled by the bending control mechanism on the in-vitro handle to bend to a certain angle; and a series of operations such as clamping, transection and anastomosis are performed on the surgical site. After the operation is completed, the elbow stapler exits the body after turning to the straight line state.

Thus, there is an urgent need for a reasonable bending control mechanism, to control the angle required for rotation of the stapler jaw, so that the operation is convenient; at the same time, the angle required for the stapler jaw is firmly locked, to prevent security risks in the unpredictable force.

SUMMARY OF THE PRESENT INVENTION

In view of the defects in the prior art, an object of the present invention is to design a simple control mechanism, to reach the purpose of making the stapler jaw turn by pulling the wrench, and simultaneously lock the stapler jaw at the selected angle. Thus, in the thoracic cavity or abdominal cavity, even the stapler jaw is subject to unpredictable forces, the jaw will not turn, thereby reducing the potential risks.

A bending control mechanism according to the present invention, comprises:
a turning power input mechanism A;
a turning transmission mechanism B;
a locking mechanism C; and
a linear power output mechanism D;
wherein:
the turning power input mechanism A and the turning transmission mechanism B which are coaxially arranged have a relative rotating angle range in a circumferential direction; the turning power input mechanism A sequentially rotates in an angle I, an angle range II and an angle III while rotating relative to the turning transmission mechanism B from one end angle to the other end angle of a relative rotating angle range;

when the turning power input mechanism A is within the angle range II, the locking mechanism C locks the turning transmission mechanism B, so that the turning transmission mechanism B and linear power output mechanism D remain relatively stationary;

when the turning power input mechanism A is at the angle I, the locking mechanism C driven by the turning power input mechanism A releases the turning transmission mechanism B; in addition, the turning transmission mechanism B is able to rotate to a first circumferential direction away from the angle range II accompanied with the turning power input mechanism A, and drive the linear power output mechanism D to displace;

when the turning power input mechanism A is at the angle III, the locking mechanism C driven by the turning power input mechanism A releases the turning transmission mechanism B; in addition, the turning transmission mechanism B is able to rotate to a second circumferential direction away from the angle range II accompanied with the turning power input mechanism A, and drive the linear power output mechanism D to displace; wherein the first circumferential direction is opposite to the second circumferential direction.

Preferably, an angle range between the angle I and the angle III form the angle range II.

Preferably, a plurality of locked positions are arranged on the turning transmission mechanism B along the circumferential direction thereof; along with rotation of the turning transmission mechanism B, the turning transmission mechanism B is able to be locked in a corresponding locked position by the locking mechanism C.

Preferably, the turning power input mechanism A is a wrench; the turning to transmission mechanism B comprises a central shaft and a locking disc arranged on the central shaft; the locking mechanism C is a slider, and the linear power output mechanism D is a rack; wherein:

a pin hole of the wrench matches with a fan-shaped hole of the central shaft via a pin; an angle of the fan-shaped hole forms the relative rotating angle range;

a plurality of switch tooth spaces are arranged on the wrench along a circumferential direction thereof;

a plurality of locking grooves are arranged on the locking disc along a circumferential direction thereof;

a launch ramp respectively matching with each of the switch tooth spaces, a locking boss respectively matching with each of the locking grooves, and a compression spring for driving the launch ramp of the slider to move into a groove chamber of each of the switch tooth spaces are arranged on the slider;

a gear arranged on the central shaft is engaged with the rack.

Preferably, when the pin is located at one end of the fan-shaped hole, the wrench is at the angle I; when the pin is located at the other end of the fan-shaped hole, the wrench is at the angle III; when the pin is located between one end and the other end of the fan-shaped hole, the wrench is within the angle range II.

Preferably, the locking boss forms locking of the locking disc by protruding into a groove chamber of one of the locking grooves defining one of the locked positions, and forms release of the locking disc by retracting from the groove chamber of one of the locking grooves.

Preferably, each locking groove comprises a straight line segment; the locking boss is engaged with the straight line segment, to lock the locking disc.

Preferably, the bending control mechanism further comprises a rotating head;

the wrench is assembled in an opening of the rotating head;

a limit boss is arranged at the opening of the rotating head; and an angle limiting groove matching with the limit boss is arranged on the wrench.

A surgical instrument comprises the bending control mechanism according to any one of the above-mentioned bending control mechanisms. The surgical instrument is a surgical stapler; the linear power output mechanism D of the bending control mechanism is connected to a jaw of the stapler.

Compared with the prior art, the present invention has the following beneficial effects:

1. By the present invention, one or more locations are able be locked in the operation, so as to bend and fix the stapler jaw to the required position, to complete the operation.

2. The invention is provided with simple mechanism and fewer parts; most of the parts are made of injection molding process, which are simple to manufacture and with low cost.

3. The bending control mechanism according to the present invention is able to be widely applied to other mechanical operating parts; and is easy to control and switch over.

BRIEF DESCRIPTION OF THE DRAWINGS

Other features, objects, and advantages of the invention will become more apparent from reading the description of non-limiting embodiments detailed with reference to the following figures.

IN THE DRAWINGS

1—wrench;
101—angle limiting groove;
102—pin hole;
103—switch tooth space;
104—cover plate;
105—boss;
2—locking disc;
201—square hole;
202—locking groove;
3—central shaft;
301—gear;
302—square face;
303—fan-shaped hole;
304—connecting groove;
4—slider;
401—compression spring;
402—compression spring groove;
403—launch ramp;
404—locking boss;
5—rack;
501—rack structure;
6—pin;
7—upper part of rotating head;
701—opening;
702—locating groove;
8—lifting ring;
801—wrench fitting groove;
802—drive ramp;
9—cam lock;
901—connection boss;
902—locating tooth;
903—pressure spring support surface;
904—driven ramp;
10—locking pressure spring.

DETAILED DESCRIPTION OF THE PREFERRED EMBODIMENT

The invention is described in detail as follows with reference to specific embodiments. The following embodiments will help provide further understanding of the invention for those skilled in the art, and not in any way limit the invention. It shall be noted that several variants and improvements is able to be made without departing from concept of the invention for ordinary persons skilled in the art. All these fall within the protection scope of the invention.

A bending control mechanism according to the invention, comprises a turning power input mechanism A;
a turning transmission mechanism B;
a locking mechanism C; and
a linear power output mechanism D;

wherein:

the turning power input mechanism A and the turning transmission mechanism B which are coaxially arranged have a relative rotating angle range in a circumferential direction; the turning power input mechanism A sequentially rotates in an angle I, an angle range II and an angle III while rotating relative to the turning transmission mechanism B from one end angle to the other end angle of a relative rotating angle range;

when the turning power input mechanism A is within the angle range II, the locking mechanism C locks the turning transmission mechanism B, so that the turning transmission mechanism B and linear power output mechanism D remain relatively stationary;

when the turning power input mechanism A is at the angle I, the locking mechanism C driven by the turning power input mechanism A releases the turning transmission mechanism B; in addition, the turning transmission mechanism B is able to rotate to a first circumferential direction away from the angle range II accompanied with the turning power input mechanism A, and drive the linear power output mechanism D to displace;

when the turning power input mechanism A is at the angle III, the locking mechanism C driven by the turning power input mechanism A releases the turning transmission mechanism B; in addition, the turning transmission mechanism B is able to rotate to a second circumferential direction away from the angle range II accompanied with the turning power input mechanism A, and drive the linear power output mechanism D to displace; wherein the first circumferential direction is opposite to the second circumferential direction.

Preferably, an angle range between the angle I and the angle III forms the angle range II.

Figure 1:
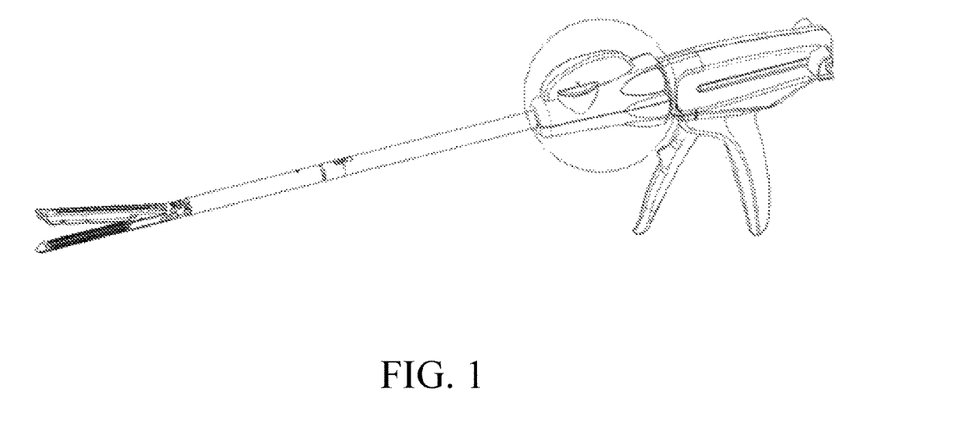
FIG. 1 is a main appearance diagram of a surgical stapler comprising a bending control mechanism.

As shown in FIG. 1, the present invention provides an endoscopic surgical stapler. The endoscopic surgical stapler comprises a tubular structure and a bending control mechanism; the tubular structure is provided with a stapler jaw at a remote end, and a near end is connected to the bending control mechanism.

Figure 2:
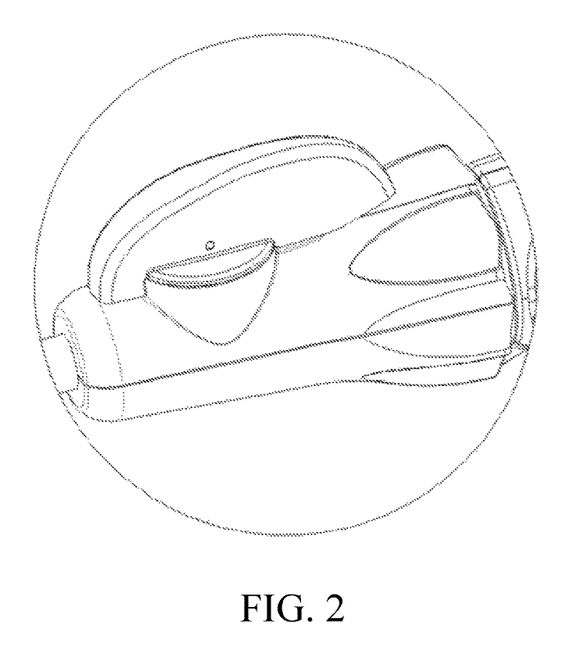
FIG. 2 is a main appearance diagram of the bending control mechanism.

FIG. 2 shows the bending control mechanism in the present invention; the bending control mechanism comprises a wrench 1 and an upper part of rotating head 7, wherein the wrench 1 is installed on the upper part of rotating head 7.

Preferably, a plurality of locked positions are arranged on the turning transmission mechanism B along the circumferential direction thereof; along with rotation of the turning transmission mechanism B, the turning transmission mechanism B is able to be locked in a corresponding locked position by the locking mechanism C.

Preferably, the turning power input mechanism A is a wrench 1; the turning transmission mechanism B comprises a central shaft 3 and a locking disc 2 arranged on the central shaft 3; the locking mechanism C is a slider 4, and the linear power output mechanism D is a rack 5; wherein:

a pin hole 102 of the wrench 1 matches with a fan-shaped hole 303 of the central shaft 3 via a pin 6; an angle of the fan-shaped hole 303 forms the relative rotating angle range;

a plurality of switch tooth spaces 103 are arranged on the wrench 1 along a circumferential direction thereof;

a plurality of locking grooves 202 are arranged on the locking disc 2 along a circumferential direction thereof;

a launch ramp 403 respectively matching with each of the switch tooth spaces 103, a locking boss 404 respectively matching with each of the locking grooves 202, and a compression spring 401 for driving the launch ramp 403 of the slider 4 to move into a groove chamber of each of the switch tooth spaces 103 are arranged on the slider 4;

a gear 301 arranged on the central shaft 3 is engaged with the rack 5.

Preferably, when the pin 6 is located at one end of the fan-shaped hole 303, the wrench 1 is at the angle I; when the pin 6 is located at the other end of the fan-shaped hole 303, the wrench 1 is at the angle III; when the pin 6 is located between one end and the other end of the fan-shaped hole 303, the wrench 1 is within the angle range II.

Preferably, the locking boss 404 forms locking of the locking disc 2 by protruding into a groove chamber of one of the locking grooves 202 defining the locked position, and forms release of the locking disc 2 by retracting from the groove chamber of one of the locking grooves 202.

Preferably, each of the locking grooves 202 comprises a straight line segment; the locking boss 404 is engaged with the straight line segment, to lock the locking disc 2.

Figure 3:
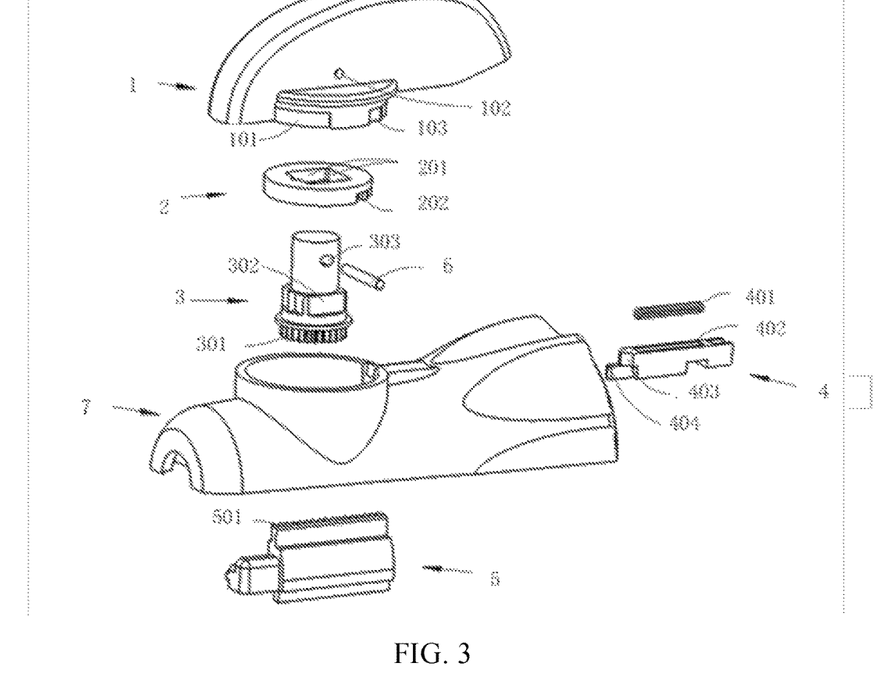
FIG. 3 is a detailed view of a split structure of the bending control mechanism in the first embodiment.

FIG. 3 shows a specific structure of the bending control mechanism; the bending control mechanism comprises the locking disc 2, the wrench 1, the slider 4 and the compression spring 401; wherein the locking disc 2 and the central shaft 3 are fixed, and provided with a series of locking grooves 202;

the wrench 1 is connected with the central shaft 3 via the pin 6; the wrench 1 is provided with a series of switch tooth spaces; the launch ramp 403 and the locking boss 404 are arranged at the remote end of the slider 4; the compression spring 401 is arranged between the slider 4 and the upper part of rotating head 7. The switch tooth spaces 103 of the wrench 1 and the locking grooves 202 of the locking disc 2 have a middle position; at this time, the stapler jaw is in a straight line state.

Figure 4:
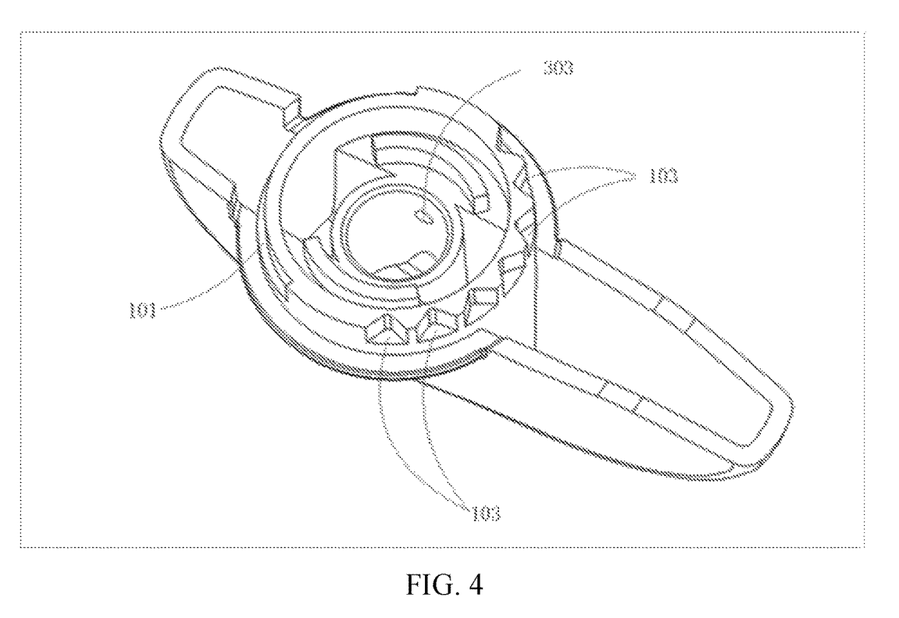
FIG. 4 is a bottom view of the bending control mechanism in the first embodiment.

More specifically, the upper part of rotating head 7 has an opening, which is able to accommodate the central shaft 3, the locking disc 2 and the wrench 1; the above-mentioned central shaft 3, locking disc 2 and wrench 1 and the opening of rotating head are arranged coaxially. The locking disc 2 is in fastening fit with a square face 302 on the central shaft 3 via a square hole 201; in some cases, the locking disc 2 and the central shaft 3 are able to be formed integrally. The pin hole 102 of the wrench 1 matches with the fan-shaped hole 303 of the central shaft 3 via the pin 6. The slider 4 is placed inside the upper part of rotating head 7, and arranged together with the upper part of rotating head 7 in a same direction; the launch ramp 403 on the slider 4 respectively matches with each of the switch tooth spaces 103 of the wrench 1; the locking boss 404 is placed in one of the locking grooves 202 of the locking disc 2. The compression spring 401 is placed in a compression spring groove 402 of the slider 4, and arranged between the boss of the upper part of rotating head 7 and the slider 4. The central shaft 3 is engaged with a rack structure 501 of the rack 5 through the gear 301 on the central shaft 3, to play a role of converting a rotary motion into a linear motion and ultimately controlling a front end of stapler to turn. In addition, an angle limiting groove 101 is arranged on the wrench 1, as shown in FIG. 4, a limit boss is arranged at the opening of the upper part of rotating head 7, to limit a rotation angle of the wrench for avoiding excessive rotation.

Preferably, the bending control mechanism further comprises a rotating head 7;

the wrench 1 is assembled in the opening of the rotating head 7;

the limit boss is arranged at the opening of the rotating head 7; and the angle limiting groove 101 matching with the limit boss is arranged on the wrench 1.

Figure 5:
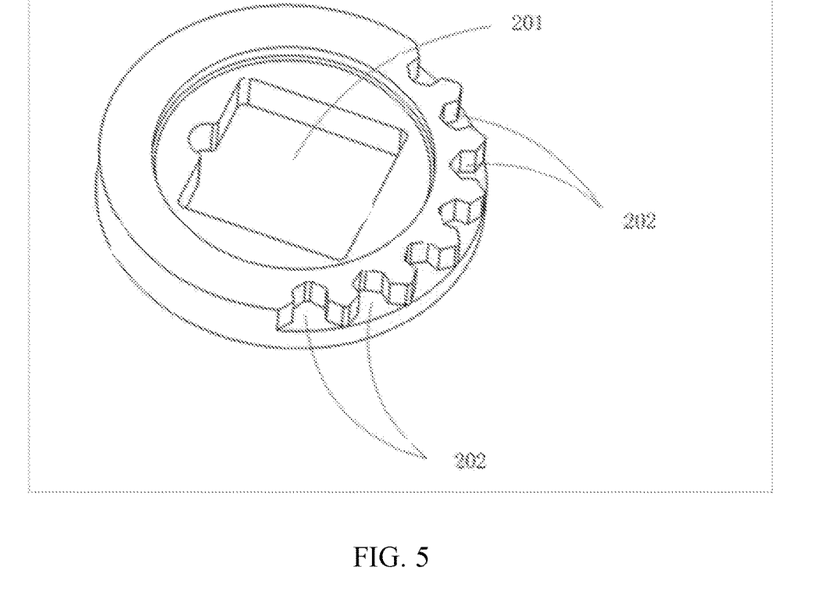
FIG. 5 is a bottom view of a locking disc in the first embodiment.

As shown in FIG. 4 and FIG. 5, each of the locking grooves 202 of the locking disc 2 comprises a straight line segment; the locking grooves 202 of the locking disc 2 are circumferentially arrayed, and an angle distribution of the locking grooves is equal; the locking grooves 202 of the locking disc 2 are respectively corresponding to the switch tooth spaces 103 of the wrench 1. An angle limiting groove 101 is arranged on the wrench 1, to ensure that the wrench rotates in a certain angle, to prevent over-rotation.

As a variant embodiment of the first embodiment provided by the invention, the angle distribution of the above-mentioned locking grooves may not be equidistant or the locking grooves 202 of the locking disc 2 are not respectively corresponding to the switch tooth spaces 103 of the wrench 1.

A surgical instrument comprises any one of the bending control mechanisms mentioned above. The surgical instrument is a surgical stapler; and the linear power output mechanism D of the bending control mechanism is connected to the jaw of the stapler.

Figure 6:
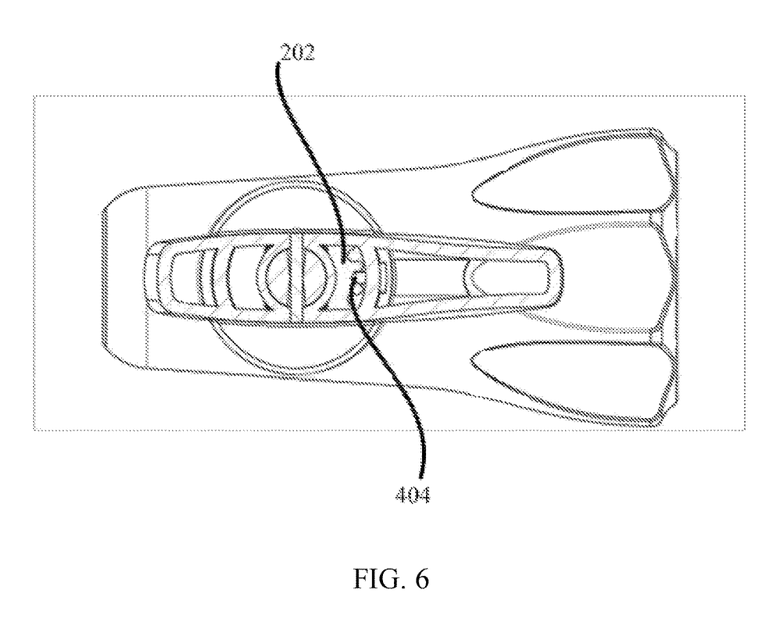
FIG. 6 is an A-A sectional view of FIG. 8.
Figure 7:
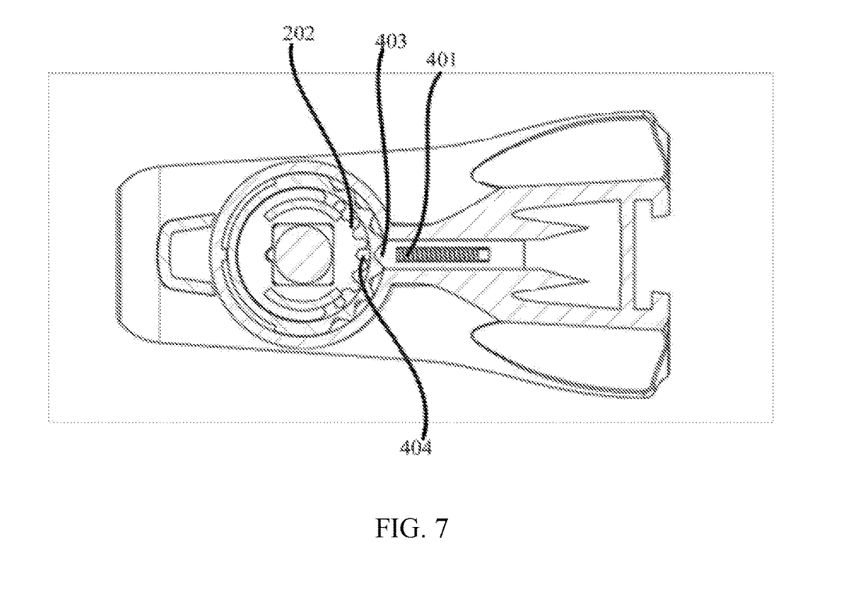
FIG. 7 is a B-B sectional view of FIG. 8.
Figure 8:
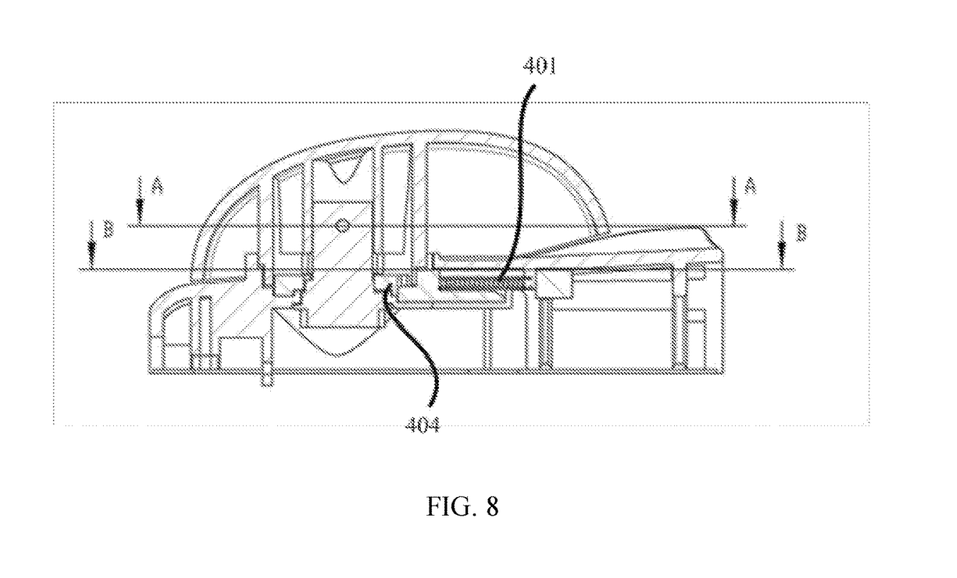
FIG. 8 is a longitudinally sectional view of the bending control mechanism when a wrench of the first embodiment is at an angle I.

As shown in FIGS. 6-14, the working principle of the above-mentioned bending control mechanisms, are specifically as follows:

As shown in FIGS. 6-8, when the pin 6 is located at one end of the fan-shaped hole 303, the wrench 1 is within the angle range I; and the compression spring 401 pushes the slider 4 to slide into one of the switch tooth spaces 103 of the wrench; at this time, the locking boss 404 of the slider 4 enters a corresponding locking groove 202 of the locking disc 2, and locks the locking disc 2 so as to lock the central shaft 3 and fix a rotation angle. Since the locking boss 404 of the slider 4 is engaged with the straight line segment of the corresponding locking groove 202 of the locking disc 2, the rotation of the gear 301 driven by the rack 5 is unable to push the slider 4 to move to achieve the purpose of locking.

Figure 9:
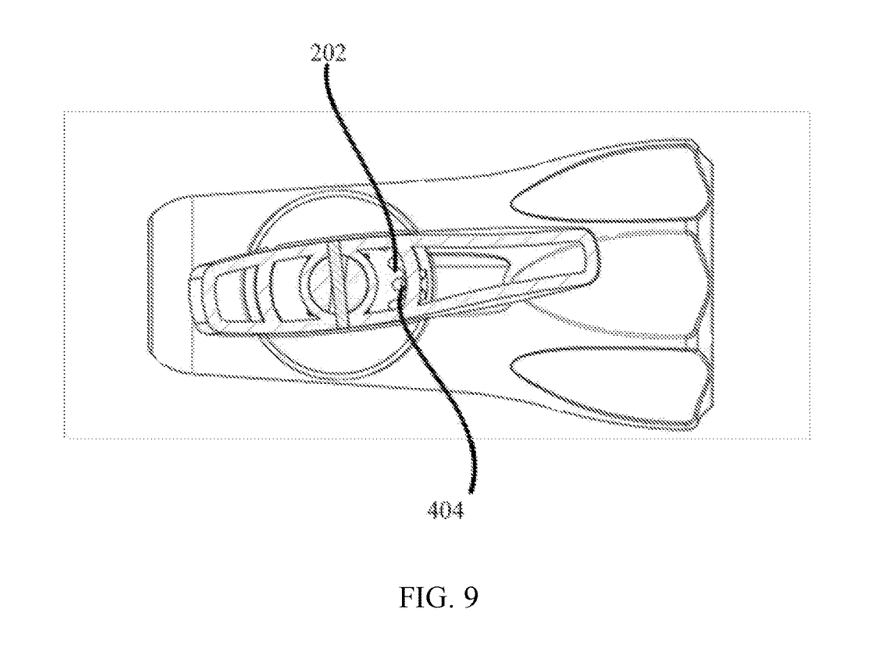
FIG. 9 is a D-D sectional view of FIG. 11.
Figure 10:
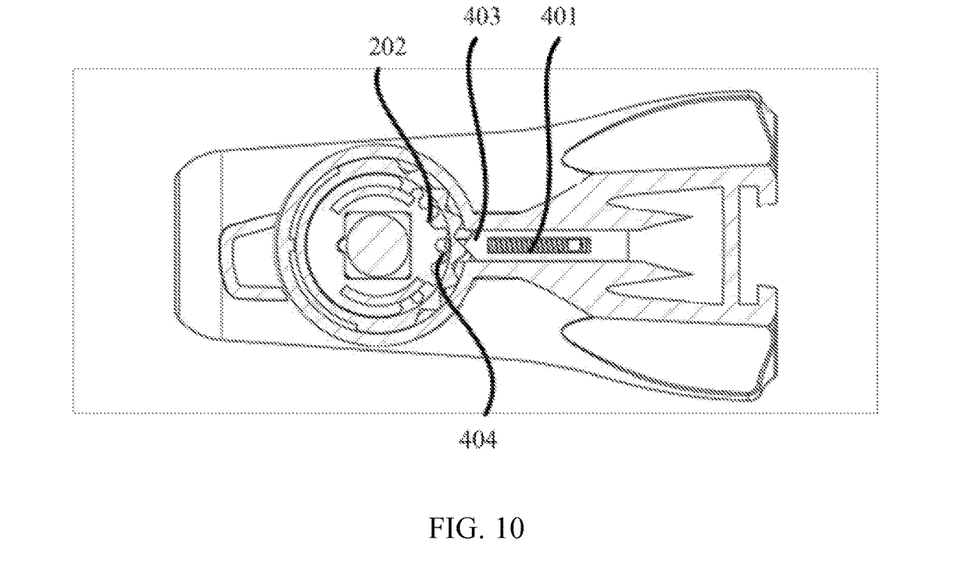
FIG. 10 is a E-E sectional view of FIG. 11.
Figure 11:
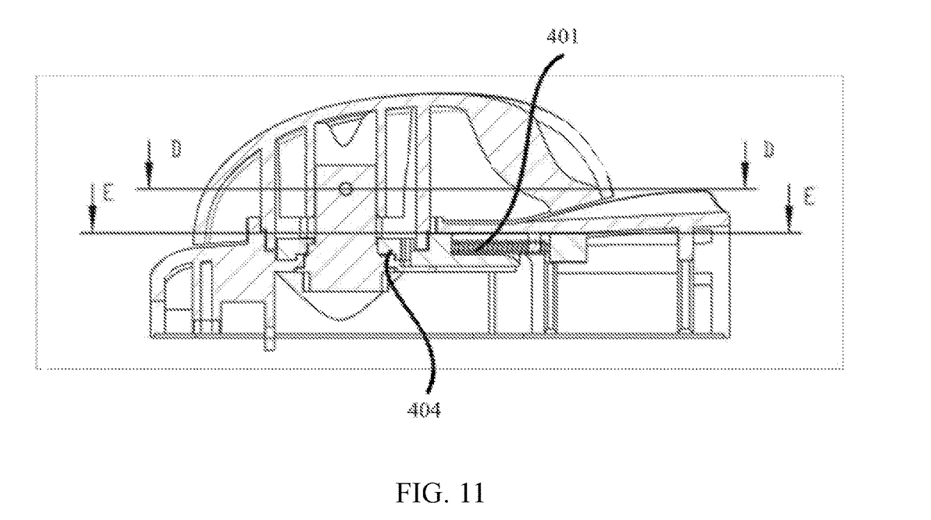
FIG. 11 is a longitudinally sectional view of the bending control mechanism when the wrench of the first embodiment is within an angle range II.

As shown in FIGS. 9-11, when the pin 6 is located between two ends of the fan-shaped hole 303, and the wrench 1 is between the angle range I and the angle range III, i.e., within the angle range II, the wrench 1 drives the pin 6 to rotate for an angle, each of the switch tooth spaces 103 of the wrench 1 respectively matches with the launch ramp 403 on the slider 4, to push out the slider 4; at this time, the matching between the locking boss 404 of the slider 4 and the corresponding locking groove 202 of the locking disc 2 is separated. When the wrench 1 is rotated continuously, the pin 6 drives the central shaft 3 to rotate through the fan-shaped hole 303, and drives the rack 5 to move forward and backward, to play a role of turning.

Figure 12:
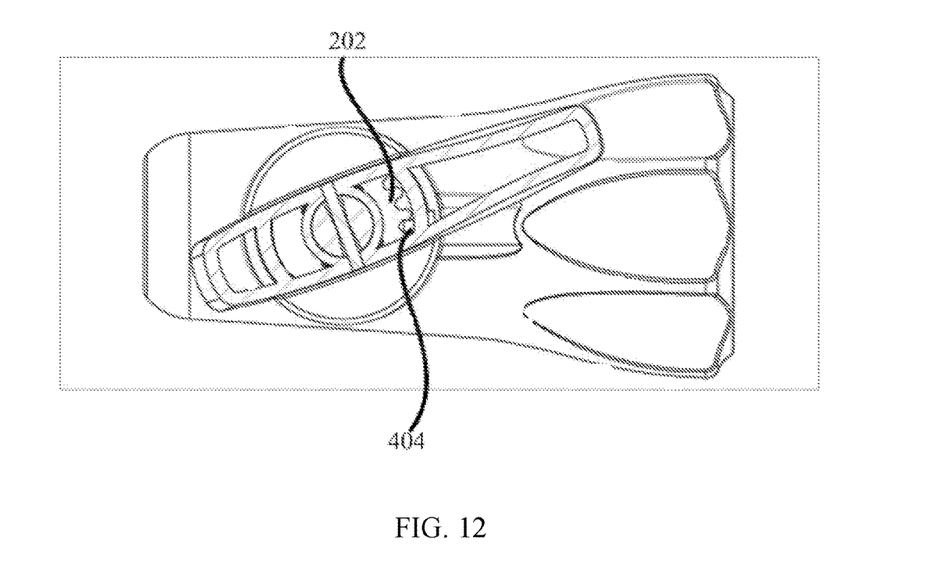
FIG. 12 is an H-H sectional view of FIG. 14.
Figure 13:
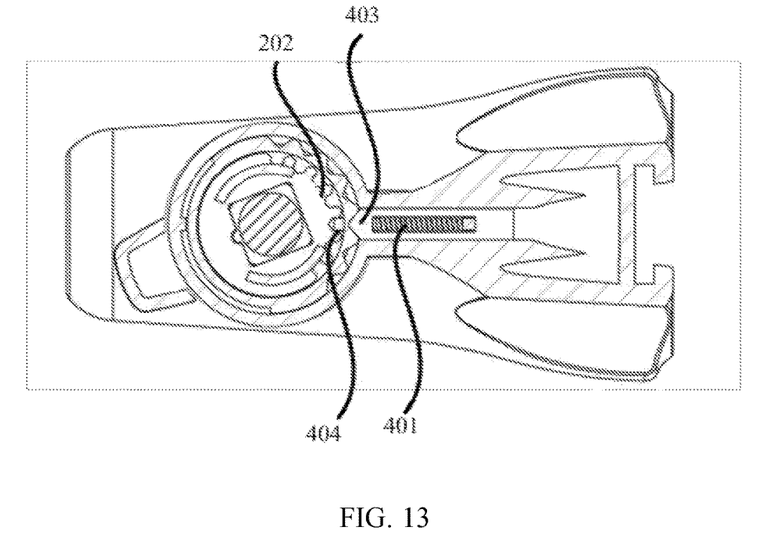
FIG. 13 is a G-G sectional view of FIG. 14.
Figure 14:
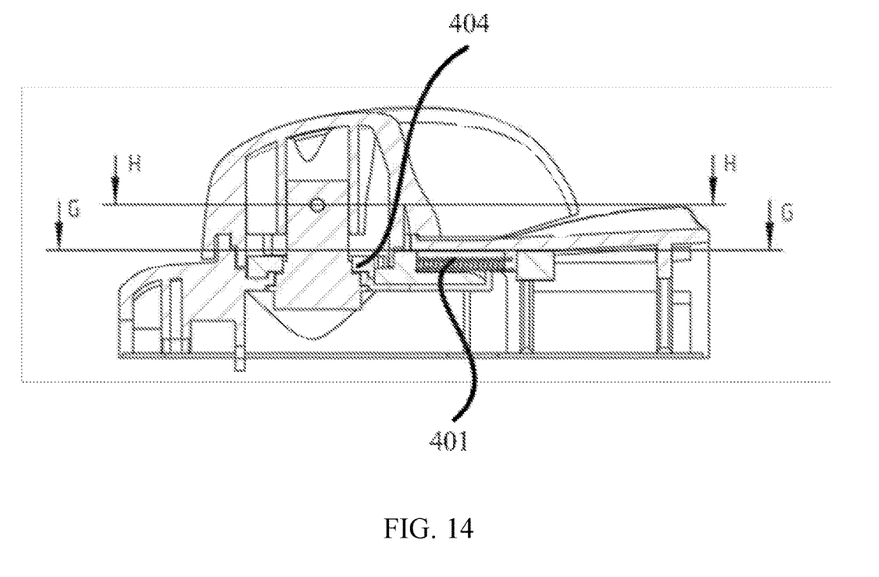
FIG. 14 is a longitudinally sectional view of the bending control mechanism when the wrench of the first embodiment is at an angle III.

As shown in FIGS. 12-14, when the pin 6 is located at the other end of the fan-shaped hole 303, the wrench 1 rotates to the next position, and the compression spring 401 pushes the slider 4 to slide into another switch tooth space 103 of the wrench; at the same time, the locking boss 404 of the slider 4 enters another corresponding locking groove 202 of the locking disc 2, and locks the locking disc 2 so as to lock the central shaft 3 and fix a rotation angle. Since the locking boss 404 of the slider 4 is engaged with the straight line segment of the corresponding locking groove 202 of the locking disc 2, the rotation of the gear 301 driven by the rack 5 is unable to push the slider 4 to move to achieve the purpose of locking.

Figure 15:
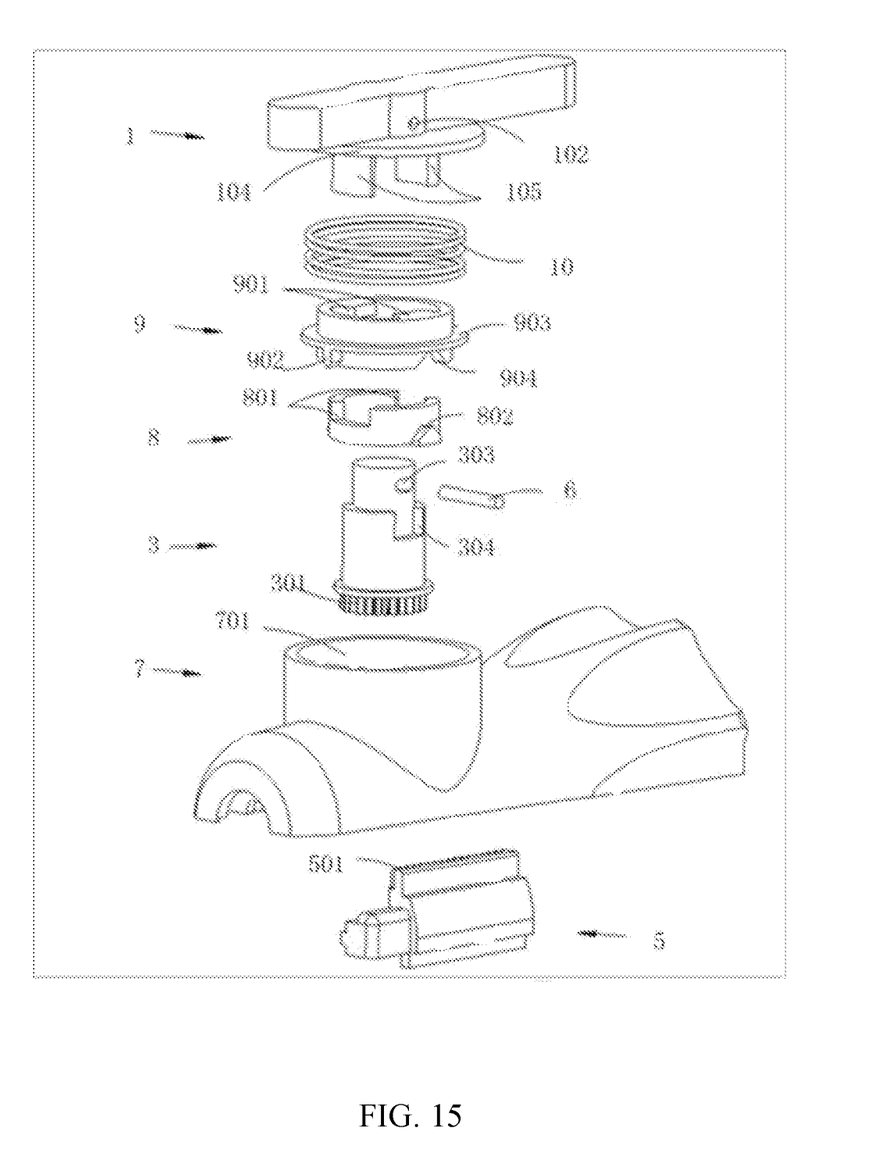
FIG. 15 is a detailed view of the split structure of the bending control mechanism in the second embodiment.

FIG. 15 shows the bending control mechanism of the second embodiment provided by the present invention; the bending control mechanism comprises a wrench 1 and an upper part of rotating head 7, wherein the wrench 1 is installed on the upper part of rotating head 7.

Specifically, the bending control mechanism comprises a wrench and a lifting ring synchronously rotates with the wrench both of which form a turning power input mechanism A; a central shaft 3 forming a turning transmission mechanism B; a cam lock 9, a locking pressure spring 10 and an upper part of rotating head 7 all of which form a locking mechanism C, wherein the cam lock 9 is engaged with the turning transmission mechanism B; and a rack 5 forming a linear power output mechanism D, wherein the rack 5 is engaged with the gear 301 arranged on the central shaft 3; further: the turning power input mechanism A and the turning transmission mechanism B which are coaxially arranged have a relative rotating angle range in a circumferential direction; the turning power input mechanism A sequentially rotates in an angle I, an angle range II and an angle III while rotating relative to the turning transmission mechanism B from one end angle to the other end angle of a relative rotating angle range; when the turning power input mechanism A is within the angle range II, the cam lock 9 driven by the locking pressure spring 10 is locked at the rotating head in meshing manner to lock the turning transmission mechanism B, so that the turning transmission mechanism B and the linear power output mechanism D remain relatively stationary; when the turning power input mechanism A is at the angle I, the cam lock 9 driven by the lifting ring 8 separates from the rotating head to release the turning transmission mechanism B; in addition, the turning transmission mechanism B is able to rotate to a first circumferential direction away from the angle range II accompanied with the turning power input mechanism A, and drive the linear power output mechanism D to displace; when the turning power input mechanism A is at the angle III, the cam lock 9 driven by the lifting ring 8 separates from the rotating head to release the turning transmission mechanism B; in addition, the turning transmission mechanism B is able to rotate to a second circumferential direction away from the angle range II accompanied with the turning power input mechanism A, and drive the linear power output mechanism D to displace; wherein the first circumferential direction is opposite to the second circumferential direction.

An opening 701 provided with a series of locating grooves 702 is arranged on the upper part of rotating head 7; the central shaft 3 is provided with a gear 301, which is connected with a stapler jaw by connecting the rack 5 and further through a connecting device placed in a tubular structure; a lifting ring 8 in coaxial arrangement with the central shaft 3 has a drive ramp 802; a cam lock 9 in coaxial arrangement with the central shaft 3 comprises a connecting boss 901 connected with the central shaft 3, a driven ramp 904 matching with the drive ramp 802 of the lifting ring 8, and a locating tooth 902; the wrench 1 matches with the lifting ring 8 via the boss 105, and connected with the central shaft 3 via the pin 6; the locking pressure spring 10 is arranged between the wrench 1 and the lifting ring 8.

An angle range between the angle I and the angle III forms the angle range II. A plurality of engagement locked positions are arranged at the opening of the rotating head in the circumferential direction; along with rotation of the cam lock 9, the rotating head is able to be meshed to a corresponding engagement locked position by the cam lock 9.

More specifically, the surgical instrument is a surgical stapler; the linear power output mechanism D of the bending control mechanism is connected to the jaw of the stapler. Wherein, each of the locating grooves 702 on the rotating head has a middle position, so that the stapler jaw is in a straight line state.

A pin hole 102 of the wrench 1 matches with a fan-shaped hole 303 of the central shaft 3 via a pin 6; an angle of the fan-shaped hole 303 forms the relative rotating angle range; the wrench 1 extends downwards out of the boss 105; the lifting ring 8 is provided with a wrench fitting groove 801; and the boss 105 is engaged in the wrench fitting groove 801.

When the pin 6 is located at one end of the fan-shaped hole 303, the wrench 1 is at the angle I; when the pin 6 is located at the other end of the fan-shaped hole 303, the wrench 1 is at the angle III; when the pin 6 is located between one end and the other end of the fan-shaped hole 303, the wrench 1 is within the angle range II.

The lifting ring 8 is provided with a drive ramp 802; the cam lock 9 is provided with a driven ramp 904, and the driven ramp 904 matches with the drive ramp 802; when the lifting ring 8 driven by the wrench 1 rotates within the angle range II, there is a relative rotation between the lifting ring 8 and the cam lock 9; when the lifting ring 8 driven by the wrench 1 rotates to the angle I and angle III, the driven ramp 904 is driven by the drive ramp 802, so that the cam lock 9 is away from the rotating head, to separate from an engagement locking with the rotating head.

The wrench 1 is provided with a cover plate 104; the cam lock 9 is provided with a pressure spring support surface 903; the locking pressure spring 10 is connected between the cover plate 104 and the pressure spring support surface 903.

A limit boss is arranged at the opening of the rotating head; and an angle limiting groove matching with the limit boss is arranged on the wrench 1. The locating grooves 702 on the rotating head are circumferentially arrayed; an angle distribution of the locating grooves 702 is not equidistant. In addition, a limit boss is arranged at opening of the rotating head, to ensure that the wrench rotates in a certain angle, to prevent over-rotation.

As a variant embodiment of the second embodiment provided by the invention, the angle distribution of the above-mentioned locking grooves is also able to be equal.

More specifically, the second embodiment of the invention is a bending control mechanism of endoscopic stapler, comprising the wrench 1, the locking pressure spring 10, the cam lock 9, the lifting ring 8, the central shaft 3, the upper part of rotating head 7, the rack 5 and the pin 6. Wherein, the upper part of rotating head 7 has an opening, which is able to accommodate the wrench 1, the locking pressure spring 10, the cam lock 9, the lifting ring 8 and the central shaft 3; the above-mentioned wrench 1, locking pressure spring 10, cam lock 9, lifting ring 8 and central shaft 3 and opening of the rotating head are arranged coaxially; a series of locating grooves 702 are arranged in the opening. The central shaft 3, the lifting ring 8 and the cam lock 9 are arranged from inside to outside; the connecting boss 901 of the cam lock 9 matches with the connecting groove 304 of the central shaft 3; the driven ramp 904 matches with the drive ramp 802 of the lifting ring 8; the locating tooth 902 is arranged in a series of locating grooves 702 on the rotating head. The boss 105 of the wrench 1 matches with the wrench fitting groove 801 of the lifting ring 8. The locking pressure spring 10 is placed between the pressure spring support surface 903 of the cam lock 9 and the cover plate 104 of the wrench 1. The pin hole 102 of the wrench 1 matches with the fan-shaped hole 303 of the central shaft 3 via the pin 6. The rack 5 is arranged in the upper part of rotating head 7, and engaged with the gear 301 of the central shaft 3.

When the wrench is rotated, the boss 105 of the wrench 1 drives the lifting ring 8 to rotate for an angle; the lifting ring 8 drives the driven ramp 904 of the cam lock 9 through the drive ramp 802, so that the cam lock 9 rises, and the locating tooth 902 and the locating grooves 702 of the upper part of rotating head 7 disengage from the engaging state; when the wrench is rotated continuously, the pin 6 drives the central shaft 3 to rotate through the fan-shaped hole 303, and the central shaft 3 drives the cam lock 9 to rotate and drives the rack 5 to move forward and backward, to play a role of turning.

When the wrench 1 rotates to the next position, the wrench 1 will be released; the locking pressure spring 10 will push the cam lock 9, to clamp the locating tooth 902 into another locating groove 702 of the upper part of rotating head 7. At this time, the cam lock 9 is able to lock the central shaft 3, so that the central shaft is unable to rotate freely. Since the locating tooth 902 of the cam lock 9 is engaged with the straight line segment of the corresponding locking groove 702 of the upper part of rotating head 7, the rotation of the gear 301 driven by the rack 5 is unable to rotate the cam lock 9 to achieve the purpose of locking.

A limit boss is arranged at the opening of the upper part of rotating head, to limit the rotation angle of the wrench and avoid excessive rotation.

Specific embodiments of the invention are described above. It shall be understood that the invention is not limited to the above-mentioned specific embodiments, and those skilled in the art are able to make different variants and modifications within the scope of the claims, and it shall not affect the substance of the invention.

What is claimed is:

1. A bending control mechanism, comprising:
   a turning power input mechanism A;
   a turning transmission mechanism B;
   a locking mechanism C; and
   a linear power output mechanism D;
   wherein:
   the turning power input mechanism A and the turning transmission mechanism B which are coaxially arranged have a relative rotating angle range along a circumferential direction; the turning power input mechanism A sequentially rotates in an angle I, an angle range II and an angle III while rotating relative to the turning transmission mechanism B from one end angle to the other end angle of a relative rotating angle range;
   when the turning power input mechanism A is within the angle range II, the locking mechanism C locks the turning transmission mechanism B, so that the turning transmission mechanism B and the linear power output mechanism D remain relatively stationary;
   when the turning power input mechanism A is at the angle III, the locking mechanism C driven by the turning power input mechanism A releases the turning transmission mechanism B; the turning transmission mechanism B is able to rotate to a second circumferential direction away from the angle range II accompanied with the turning power input mechanism A, and drive the linear power output mechanism D to displace; wherein the first circumferential direction is opposite to the second circumferential direction;
   the turning power input mechanism A is a wrench (1); the turning transmission mechanism B comprises a central shaft (3) and a locking disc (2) arranged on the central shaft (3); the locking mechanism C is a slider (4), and the linear power output mechanism D is a rack (5);
   a pin hole (102) of the wrench (1) matches with a fan-shaped hole (303) of the central shaft (3) via a pin (6); an angle of the fan-shaped hole (303) forms the relative rotating angle range;

a plurality of switch tooth spaces (103) are arranged on the wrench (1) along a circumferential direction thereof;
a plurality of locking grooves (202) are arranged on the locking disc (2) along a circumferential direction thereof;
a launch ramp (403) respectively matching with each of the switch tooth spaces (103), a locking boss (404) respectively matching with each of the locking grooves (202), and a compression spring (401) for driving the launch ramp (403) of the slider (4) to move into a groove chamber of each of the switch tooth spaces (103) are arranged on the slider (4);
a gear (301) arranged on the central shaft (3) is engaged with the rack (5).

2. The bending control mechanism according to claim 1, wherein an angle range between the angle I and the angle III forms the angle range II.

3. The bending control mechanism according to claim 2, wherein when the pin (6) is located at one end of the fan-shaped hole (303), the wrench (1) is at the angle I; when the pin (6) is located at the other end of the fan-shaped hole (303), the wrench (1) is at the angle III; when the pin (6) is located between one end and the other end of the fan-shaped hole (303), the wrench (1) is within the angle range II.

4. The bending control mechanism according to claim 2, wherein the locking boss (404) forms locking of the locking disc (2) by protruding into a groove chamber of one of the locking grooves (202) forming one of the locked positions, and forms release of the locking disc (2) by retracting from the groove chamber of one of the locking grooves (202).

5. The bending control mechanism according to claim 4, wherein each of the locking grooves (202) comprises a straight line segment; the locking boss (404) is engaged with the straight line segment, to lock the locking disc (2).

6. The bending control mechanism according to claim 1, wherein a plurality of locked positions are arranged on the turning transmission mechanism B in the circumferential direction; along with rotation of the turning transmission mechanism B, the turning transmission mechanism B is able to be locked in a corresponding locked position by the locking mechanism C.

7. The bending control mechanism according to claim 6, wherein when the pin (6) is located at one end of the fan-shaped hole (303), the wrench (1) is at the angle I; when the pin (6) is located at the other end of the fan-shaped hole (303), the wrench (1) is at the angle III; when the pin (6) is located between one end and the other end of the fan-shaped hole (303), the wrench (1) is within the angle range II.

8. The bending control mechanism according to claim 6, wherein the locking boss (404) forms locking of the locking disc (2) by protruding into a groove chamber of one of the locking grooves (202) forming one of the locked positions, and forms release of the locking disc (2) by retracting from the groove chamber of one of the locking grooves (202).

9. The bending control mechanism according to claim 8, wherein each of the locking grooves (202) comprises a straight line segment; the locking boss (404) is engaged with the straight line segment, to lock the locking disc (2).

10. The bending control mechanism according to claim 1, wherein when the pin (6) is located at one end of the fan-shaped hole (303), the wrench (1) is at the angle I; when the pin (6) is located at the other end of the fan-shaped hole (303), the wrench (1) is at the angle III; when the pin (6) is located between one end and the other end of the fan-shaped hole (303), the wrench (1) is within the angle range II.

11. The bending control mechanism according to claim 1, wherein the locking boss (404) forms locking of the locking disc (2) by protruding into a groove chamber of one of the locking grooves (202) forming one of the locked positions, and forms release of the locking disc (2) by retracting from the groove chamber of one of the locking grooves (202).

12. The bending control mechanism according to claim 11, wherein each of the locking grooves (202) comprises a straight line segment; the locking boss (404) is engaged with the straight line segment, to lock the locking disc (2).

13. The bending control mechanism according to claim 1, further comprising a rotating head (7);
the wrench (1) is assembled in an opening of the rotating head (7);
a limit boss is arranged at the opening of the rotating head (7); and an angle limiting groove (101) matching with the limit boss is arranged on the wrench (1).

14. A surgical instrument, comprising a bending control mechanism which comprises:
a turning power input mechanism A;
a turning transmission mechanism B;
a locking mechanism C; and
a linear power output mechanism D;
wherein:
the turning power input mechanism A and the turning transmission mechanism B which are coaxially arranged have a relative rotating angle range along a circumferential direction; the turning power input mechanism A sequentially rotates in an angle I, an angle range II and an angle III while rotating relative to the turning transmission mechanism B from one end angle to the other end angle of a relative rotating angle range;
when the turning power input mechanism A is within the angle range II, the locking mechanism C locks the turning transmission mechanism B, so that the turning transmission mechanism B and the linear power output mechanism D remain relatively stationary;
when the turning Power input mechanism A is at the angle I, the locking mechanism C driven by the turning power input mechanism A releases the turning transmission mechanism B; the turning transmission mechanism B is able to rotate to a first circumferential direction away from the angle range II accompanied with the turning power input mechanism A, and drive the linear power output mechanism D to displace;
when the turning power input mechanism A is at the angle III, the locking mechanism C driven by the turning power input mechanism A releases the turning transmission mechanism B; the turning transmission mechanism B is able to rotate to a second circumferential direction away from the angle range II accompanied with the turning power input mechanism A, and drive the linear power output mechanism D to displace;
wherein the first circumferential direction is opposite to the second circumferential direction;
the surgical instrument is a surgical stapler, the linear power output mechanism D of the bending control mechanism is connected to a law of the stapler;
the turning power input mechanism A is a wrench (1); the turning transmission mechanism B comprises a central shaft (3) and a locking disc (2) arranged on the central shaft (3); the locking mechanism C is a slider (4), and the linear power output mechanism D is a rack (5);
a pin hole (102) of the wrench (1) matches with a fan-shaped hole (303) of the central shaft (3) via a pin (6); an angle of the fan-shaped hole (303) forms the relative rotating angle range;

a plurality of switch tooth spaces (103) are arranged on the wrench (1) along a circumferential direction thereof;

a plurality of locking grooves (202) are arranged on the locking disc (2) along a circumferential direction thereof;

a launch ramp (403) respectively matching with each of the switch tooth spaces (103), a locking boss (404) respectively matching with each of the locking grooves (202), and a compression spring (401) for driving the launch ramp (403) of the slider (4) to move into a groove chamber of each of the switch tooth spaces (103) are arranged on the slider (4);

a gear (301) arranged on the central shaft (3) is engaged with the rack (5).

15. The surgical instrument according to claim 14, wherein when the pin (6) is located at one end of the fan-shaped hole (303), the wrench (1) is at the angle I; when the pin (6) is located at the other end of the fan-shaped hole (303), the wrench (1) is at the angle III; when the pin (6) is located between one end and the other end of the fan-shaped hole (303), the wrench (1) is within the angle range II.

\* \* \* \* \*